US006342381B1

(12) United States Patent
Jaquess

(10) Patent No.: US 6,342,381 B1
(45) **Date of Patent: *Jan. 29, 2002**

(54) ENZYME STABILIZATION WITH PRE-SUPERPOLYAMIDE OR PRE-FIBER-FORMING POLYAMIDE OLIGOMERS

(75) Inventor: Percy A. Jaquess, Tigrett, TN (US)

(73) Assignee: Buckman Laboratories Internationals, Inc., Memphis, TN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/031,830

(22) Filed: Feb. 27, 2002

(51) Int. Cl.[7] .......... C12N 9/96; C12N 11/08; C12N 9/20; C12N 9/24; C12N 9/50

(52) U.S. Cl. .......... 435/188; 435/180; 435/198; 435/200; 435/201; 435/209; 435/219

(58) Field of Search .......... 435/188, 174, 435/177, 178, 180, 198, 200, 201, 209, 219; 530/402

(56) References Cited

U.S. PATENT DOCUMENTS

| | | | | |
|---|---|---|---|---|
| 2,281,576 A | | 5/1942 | Hanford | 260/78 |
| 3,944,470 A | | 3/1976 | Diehl et al. | 195/63 |
| 3,950,277 A | | 4/1976 | Stewart et al. | 252/541 |
| 4,011,169 A | | 3/1977 | Diehl et al. | 252/95 |
| 4,169,817 A | | 10/1979 | Weber | 252/545 |
| 4,243,543 A | | 1/1981 | Guilbert et al. | 252/105 |
| 4,272,396 A | | 6/1981 | Fukano et al. | 252/174.12 |
| 4,318,818 A | | 3/1982 | Letton et al. | 252/174.12 |
| 4,548,727 A | | 10/1985 | Shaer | 252/171 |
| 4,615,985 A | * | 10/1986 | Deutsch et al. | 436/531 |
| 4,711,739 A | | 12/1987 | Kandathil | 252/139 |
| 4,715,990 A | | 12/1987 | Crossin | 252/551 |
| 4,801,544 A | | 1/1989 | Munk | 435/188 |
| 4,908,150 A | | 3/1990 | Hessel et al. | 252/174.12 |
| 5,082,585 A | | 1/1992 | Hessel et al. | 252/174.12 |
| 5,356,800 A | | 10/1994 | Jaquess | 435/188 |
| 5,643,721 A | * | 7/1997 | Spring et al. | 436/6 |
| 5,691,154 A | | 11/1997 | Callstrom et al. | 435/7.6 |
| 5,880,252 A | * | 3/1999 | Kim et al. | 528/332 |

FOREIGN PATENT DOCUMENTS

| | | |
|---|---|---|
| EP | 0 126 505 A1 | 11/1984 |
| EP | 0 351 162 A1 | 1/1990 |
| EP | 0 352 244 A2 | 1/1990 |
| WO | WO 94/29424 | 12/1994 |

OTHER PUBLICATIONS

J.C. Makemson et al., "Stabilization of Luciferase Intermediates by Fatty Amines, Amides, and Nitriles", Archives Of Biochemistry And Biophysics, vol. 294, No. 2, pp. 361–366(1992).

R.J. Gaymans, "The Synthesis and Some Properties of Nylon 4,T", Journal Of Polymer Science: Polymer Chemistry Edition, vol. 23, pp. 1599–1605 (1985).

E. Roerdink et al., "Preparation and Properties of High Molar Mass Nylon–4, 6: A New Development in Nylon Polymers", Polymer, vol. 26, pp. 1582–1588 (1985).

S. Say–Kyoun Ow, "Biological De–Inking Methods of Newsprint Wastepaper", World Pulp and Paper Technology, pp. 63–66 (1992).

D. Y. Prasad et al., "Enzyme Deinking of Black and White Letterpress Printed Newsprint Waste", Progress in Paper Recycling, vol. 1, No. 3, pp. 21–30 (1992).

D.J. Senior et al., "Reduction in Chlorine Use During Bleaching of Kraft Pulp Following Xylanase Treatment", Bleaching: Tappi Press Anthology of Published Papers, 1991–1992 (Jameel, H., ed.), Chapter 4: 274–279 (1993; TAPPI Press).

K. Fischer and K. Messner, "Reducing Troublesome Pitch in Pulp Mills By Lipolytic Enzymes", Tappi Journal, pp. 130–134 (Feb. 1992).

J. Christner, "The Use of Lipases in the Beamhouse Processes", J. A. L. C. A., vol. 87, pp. 128–140 (1992).

R. E. Kirk, Encyclopedia of Chemical Technology, vol. 10, pp. 153–154 (1953).

Hans R. Kricheldorf, Handbook of Polymer Synthesis: Institute for Technical Macromolecular Chemistry, University of Hamburg, Hamburg, Germany; Marcel Dekker; Chapter 14: pp. 807–925 (1992).

Database WPI 82–89861E, Week 8242, "Enzymatic Detergent Composition Containing Specified Enzyme Stabiliser Mixture, and Surfactants, Salts, Scent and Bleach to Increase Stability", (1981).

Database WPI 83–62719K, Week 8326, "Enzyme Fixing Process—Comprises Quaternising Polyamide with Tert. Nitrogen and Bonding with Enzyme", (1983).

* cited by examiner

*Primary Examiner*—David M. Naff
(74) *Attorney, Agent, or Firm*—Morgan, Lewis & Bockius LLP

(57) ABSTRACT

Enzymes are stabilized with pre-superpolyamide or pre-fiber-forming polyamide oligomers having a polymer chain backbone containing only secondary amide linkages. The polyamide is combined with an enzyme such as in a liquid enzymatic composition or where the enzyme is in a non-fluid state such as a powder to improve stability and shelf-life of the enzyme. The polyamide oligomer is a condensation product of at least one dibasic acid and at least one diamine. The dibasic acid may be a saturated or unsaturated $C_3$–$C_{10}$ dicarboxylic acid, and the diamine may be 1,2-diaminoethane, 1,3-diaminopropane, 1,4-diaminobutane, 1,5-diaminopentane, 1,6-diaminohexane, 1,8-diaminooctane or 1,10-diaminodecane. Enzymes stabilized include proteases, xylanases, amylases, cellulases and lipases.

18 Claims, No Drawings

ENZYME STABILIZATION WITH PRE-SUPERPOLYAMIDE OR PRE-FIBER-FORMING POLYAMIDE OLIGOMERS

BACKGROUND OF THE INVENTION

1. Field of the Invention

The invention relates to polyamide oligomers capable of stabilizing one or more enzymes. The invention also relates to stabilized enzymatic compositions containing such polyamide oligomers. Enzymes stabilized by the polyamide oligomers of the invention exhibit improved storage, shelf-life and dispersibility at high and low temperatures.

2. Description of the Related Art

The use of enzymes and liquid enzymatic compositions in industry and in the commercial marketplace has grown rapidly over the last several years. For example, many enzymes and liquid enzymatic compositions have been associated with liquid detergents and have shown utility as solubilizing and cleaning formulations. The enzymes used, alone or in liquid enzymatic compositions, encompass a wide variety of enzyme classes and can be acid, alkaline or neutral, depending upon the pH range in which they are active.

Proteases are a well-known class of enzymes frequently utilized in a wide variety of industrial applications where they act to hydrolyze peptide bonds in proteins and proteinaceous substrates. Commercially, the greatest uses of proteases are made in the laundry detergent industry, where they help to remove protein based stains such as blood or egg stains, and in the cheese making industry, where they aid in curdling milk. Proteases are also used as meat tenderizers, for softening leather, for modifying food ingredients, and for flavor development. Liquid enzymatic compositions containing alkaline proteases have also been shown to be useful as dispersants of bacterial films, algal and fungal mats in cooling tower waters, and metalworking fluid containment bays.

Acid proteases include the microbial rennets, rennin (chymosin), pepsin, and fungal acid proteases. Neutral proteases include trypsin, papain, bromelain/ficin, and bacterial neutral protease. Alkaline proteases include subtilisin and related proteases. Commercial liquid enzymatic compositions containing proteases are available under the names RENNILASE®, "PTN" (Pancreatic Trypsin NOVO), "PEM" (Proteolytic Enzyme Mixture), NEUTRASE®, ALCALASE®, ESPERASE®, and SAVINASE™ which are all supplied by Novo Nordisk Bioindustrials, Inc. of Danbury, Conn. Another commercial liquid enzymatic composition containing proteases is available under the name HT-Proteolytic supplied by Solvay Enzyme Products.

Another class of enzyme known as amylases have also been utilized in many industrial and commercial processes in which they act to catalyze or accelerate the hydrolysis of starch. Amylases are used largely in the corn syrup industry for the production of glucose syrups, maltose syrups, and a variety of other more refined end products of starch hydrolysis such as high fructose syrups. As a class they include alpha-amylase, beta-amylase, amyloglucosidase (glucoamylase), fungal amylase, and pullulanase. Commercial liquid enzymatic compositions containing amylases are available under the names BAN, TERMAMYL®, AMG, FUNGAMYL®, and PROMOZYME™, which are supplied by Novo Nordisk, and Diazyme L-200, a product of Solvay Enzyme Products.

Other commercially valuable enzyme classes are those which affect the hydrolysis of fiber. These classes include cellulases, hemicellulases, pectinases, and beta-glucanases. Cellulases are enzymes that degrade cellulose, a linear glucose polymer occurring in the cell walls of plants. Hemicellulases are involved in the hydrolysis of hemicellulose which, like cellulose, is a polysaccharide found in plants. The pectinases are enzymes involved in the degradation of pectin, a carbohydrate whose main component is a sugar acid. Beta-glucanases are enzymes involved in the hydrolysis of beta-glucans which are also similar to cellulose in that they are linear polymers of glucose. In a commercial context, these enzymes have utility to a greater or lesser degree in manufacturing processes dependent on fiber degradation.

Cellulases have reported utility in the de-inking process of old newsprint (ONP) wastepaper, eliminating the need for any surfactants and alkaline chemicals. The enzymes dislodge inks from fiber surfaces and disperse ink particles to a finite size. S. Say-Kyoun Ow, "Biological De-Inking Methods of Newsprint Wastepaper", *World Pulp and Paper Technology,* 63–64 (1992). Collectively, cellulases include endocellulase, exocellulase, exocello-biohydrolase, and celloblase. Commercial liquid enzymatic compositions containing cellulases are available under the names CELLUCLAST® and NOVOZYM® 188 which are both supplied by Novo Nordisk.

Hemicellulases are also used in the de-inking process to dislodge ink particles from the fiber surface of ONP. D. Y. Prasad et al., "Enzyme Deinking of Black and White Letterpress Printed Newsprint Waste", *Progress in Paper Recycling,* 21–22 (1992). Additionally, hemicellulases, such as the xylanases, are employed in the pulp bleaching process. Xylanase pretreatment of kraft pulps has resulted in major reductions in bleaching chemical requirements, such as molecular chlorine, and has also improved pulp quality as reflected by higher brightness ceilings. D. J. Senior et al., "Reduction in Chlorine Use During Bleaching of Kraft Pulp Following Xylanase Treatment", *Bleaching: Tappi Press Anthology of published Papers,* 1991–1992 (Jameel, H., ed.), Chapter 4: 274–279 (1993; TAPPI Press). PULPZYME® product, available from Novo Nordisk, and ECOPULP® product, from Alko Biotechnology, are two examples of commercially available liquid enzymatic compositions containing xylanase-based bleaching enzymes.

As a class, hemicellulases include hemicellulase mixture and galactomannanase. Commercial liquid enzymatic compositions containing hemicellulases are available as PULPZYME® from Novo, ECOPULP® from Alko Biotechnology and NOVOZYM® 280 and GAMANASE™, which are both products of Novo Nordisk.

The pectinases are used commercially to weaken cell walls and enhance extraction of fruit juice, as well as to aid in decreasing viscosity and preventing gelation in these extracts. Pectinases consist of endopolygalacturonase, exopolygalacturonase, endopectate lyase (transeliminase), exopectate lyase (transeliminase), and endopectin lyase (transeliminase). Commercial liquid enzymatic compositions containing pectinases are available under the names PECTINEX™ Ultra SP and PECTINEX™, both supplied by Novo Nordisk.

The beta-glucanases are of importance in malting and brewing industries where modification of barley cell walls containing beta-glucans is necessary. Beta-glucanases include lichenase, laminarinase, and exoglucanase. Commercial liquid enzymatic compositions containing beta-glucanases are available under the names NOVOZYM® 234, CEREFLO®, BAN, FINIZYM®, and CEREMIX®, all of which are supplied by Novo Nordisk.

Two additional classes of industrially and commercially useful enzymes are lipases and phospholipases. Lipases and phospholipases are esterase enzymes which hydrolyze fats and oils by attacking the ester bonds in these compounds. Lipases act on triglycerides, while phospholipases act on phospholipids. In the industrial sector, lipases and phospholipases represent the commercially available esterases, and both currently have a number of industrial and commercial applications.

In the pulp and paper industry, liquid enzyme preparations containing lipases have proven to be particularly useful in reducing pitch deposits on rolls and other equipment during the production process. For example, the treatment of unbleached sulfite pulp with lipases prior to bleaching with chlorine to reduce the content of chlorinated triglycerides, which are reportedly the cause of pitch deposition during the paper manufacturing process, has been reported. K. Fischer and K. Messher, "Reducing Troublesome Pitch in Pulp Mills By Lipolytic Enzymes", *Tappi Journal,* 130 (1992). Novo Nordisk markets two liquid enzyme preparations under the names RESINASE™ A and RESINASE™ A 2X, both of which, under certain conditions, reportedly reduce pitch deposits significantly by breaking down wood resins in pulp.

Another important use of lipases is to degrease hides and pelts in the leather making process. Alkaline lipases are used in conjunction with special proteases and emulsifying systems to aid degreasing, as well as to improve the soaking and liming effect in leather making. J. Christher, "The Use of Lipases in the Beamhouse Processes", *J.A.L.C.A.* 87, 128 (1992).

Lipases have also been used for the development of flavors in cheese and to improve the palatability of beef tallow to dogs. In nonaqueous systems, lipases have been employed to synthesize esters from carboxylic acids and alcohols. Commercial liquid enzymatic compositions containing lipases are available under the names Lipolase 100, Greasex 50L, PALATASE™ A, PALATASE™ M, and NIPOZYME™ which are all supplied by Novo Nordisk.

With respect to the commercially useful phospholipases, pancreatic phospholipase A2 has been used to convert lecithin into lysolecithin. Lysolecithin reportedly is an excellent emulsifier in the production of mayonnaise and the baking of bread. Commercially, phospholipase A2 is available in a liquid enzymatic composition sold as LECITASE™ by Novo Nordisk.

Another commercially valuable class of enzymes are the isomerases which catalyze conversion reactions between isomers of organic compounds. The isomerases are particularly important in the high fructose corn syrup industry. For example, the aldose-ketose isomerase reaction, catalyzed by glucose isomerase, involves the conversion of glucose to fructose and is just one of three key enzyme reactions in the industry. SWEETZYME® product is a liquid enzymatic composition containing glucose isomerase which is supplied by Novo Nordisk.

Redox enzymes are enzymes that act as catalysts in chemical oxidation/reduction reactions and, consequently, are involved in the breakdown and synthesis of many biochemicals. Currently, many redox enzymes have not gained a prominent place in industry since most redox enzymes require the presence of a cofactor. However, where cofactors are an integral part of an enzyme or do not have to be supplied, redox enzymes are commercially useful, particularly in the food processing industry.

The redox enzyme glucose oxidase is used to prevent unwanted browning reactions affecting food color and flavor. Glucose oxidase is also used as an "oxygen scavenger" to prevent the development of off-flavors in juices and to preserve color and stability in certain sensitive food ingredients. The redox enzyme catalase has been utilized to decompose residual hydrogen peroxide used as a sterilizing agent. A third redox enzyme, lipoxidase (lipoxygenase), found naturally in soya flour and not usually purified for industrial use, is used in baking, not only to obtain whiter bread, but also to reverse the dough-softening effects caused by certain agents. Other redox enzymes have possible applications ranging from the enzymatic synthesis of steroid derivatives to use in diagnostic tests. These redox enzymes include peroxidase, superoxide dismutase, alcohol oxidase, polyphenol oxidase, xanthine oxidase, sulfhydryl oxidase, hydroxylases, cholesterol oxidase, laccase, alcohol dehydrogenase, and steroid dehydrogenases.

When enzymes, such as those described above, are prepared or sold for use in industrial processes, they generally are formulated into liquid enzymatic compositions designed for a particular process. These liquid enzymatic compositions, however, have historically been plagued with problems such as chemical instability which can result in the loss of enzymatic activity, particularly upon storage. This critical problem of loss of enzymatic activity due to storage has particularly affected the liquid detergent industry. It is not uncommon to have industrial products, such as liquid enzymatic compositions, stored in warehouses in various climates around the world where the product is subjected to a temperature that may range from freezing to above 50° C. for extended periods. After storage at temperature extremes ranging from 0° C. to 50° C. for many months, most liquid enzymatic compositions lose from 20 to 100 percent of their enzymatic activity due to enzyme instability.

Various attempts have been made to stabilize enzymes contained in liquid enzymatic compositions. Attempts to increase the stability of liquid enzymatic compositions using formulations containing alcohols, glycerol, dialkylglycolethers, block copolymers, graft copolymers of polyesters from ethylene glycol or ethylene oxide and mixtures of these and other compounds have had only marginal success, even in moderate storage temperature ranges.

In U.S. Pat. No. 5,082,585, which was a continuation-in-part of U.S. Pat. No. 4,908,150, enzymatic liquid detergent compositions are described which comprise lipolytic enzymes. The stability of the lipolytic enzymes in the compositions is significantly improved by inclusion of particular nonionic ethylene glycol containing copolymers. The polymers comprise ethylene glycol or ethylene oxide copolymerized with difunctional acids or vinylic based copolymers. The copolymers can be predominantly linear block or random or can be graft copolymers with pendant side chains. However, the stability data exemplified for these polymers showed that they only stabilized lipolase for a maximum of 47.7 days at 37° C.

In U.S. Pat. No. 4,801,544, a system of ethylene glycol and ethoxylated linear alcohol nonionic surfactant with hydrocarbon solvent utilized as a stabilizer and the encapsulation of enzymes in micelles within the solvent/surfactant mixture is described. The water content of the composition was kept at less than 5 percent, and enzyme stability was checked at 35°, 70°, and 100° F.

In U.S. Pat. No. 4,715,990, a soil release promoting enzyme-containing nonionic detergent based liquid detergent is described. The detergent comprises a synthetic organic nonionic detergent, a higher fatty alcohol polyethoxylate sulfate, a particular type of soil release promoting copolymer of polyethylene terephthalate and polyoxyethylene terephthalate, a proportion of enzyme(s) sufficient to enzymatically hydrolyze proteinaceous and/or amylaceous soils on fabrics during washing with an aqueous washing solution of the liquid detergent, a stabilizing proportion of a stabilizer for the enzyme(s), and an aqueous medium.

The stabilization of an aqueous enzyme preparation using certain esters has been described in U.S. Pat. No. 4,548,727. The ester used as a stabilizer has the formula RCOOR', where R is an alkyl of from one to three carbons or hydrogen, and R' is an alkyl of from one to six carbons. The ester is present in the aqueous enzyme preparation in an amount from 0.1 to about 2.5% by weight.

U.S. Pat. No. 4,318,818 describes a stabilizing system for aqueous enzyme compositions where the stabilizing system comprises calcium ions and a low molecular weight carboxylic acid or its salt. The pH of the stabilizing system is from about 6.5 to about 10.0.

In U.S. Pat. No. 3,950,277 compositions comprising a lipolytic enzyme, a lipase activator selected from the group consisting of water-soluble naphthalene sulfonates; water-soluble polyoxyalkylene derivatives of ethylenediamine; and water-soluble acyl-amino acid salts are described.

In U.S. Pat. Nos. 3,944,470 and 4,011,169 enzyme-containing compositions containing an enzyme and certain aminated polysaccharides are described. Enzymatic detergent compositions containing certain organic surface-active agents in combination with enzymes and aminated polysaccharides are described as well.

U.S. Pat. No. 4,272,396 describes enzyme-containing detergent compositions containing as essential ingredients: α-olefin sulfonates, polyethylene glycols and enzymes. U.S. Pat. No. 4,243,543 describes the stabilization of liquid proteolytic enzyme-containing detergent compositions by adding an antioxidant and a hydrophilic polyol to the composition while stabilizing the pH of the composition.

U.S. Pat. No. 4,169,817 describes a liquid cleaning composition containing stabilized enzymes. The composition is an aqueous solution containing from 10% to 50% by weight of solids and including detergent builders, surface active agents, an enzyme system derived from *Bacillus subtilis* and an enzyme stabilizing agent. The stabilizing agents comprise highly water soluble sodium or potassium salts and/or water soluble hydroxy alcohols and enable the solution to be stored for extended periods without deactivation of the enzymes.

Other detergent compositions have also been described. U.S. Pat. No. 4,711,739 describes water-in-oil emulsion-type prespotter laundry compositions containing enzymes and specific polyester or polyester polyols. European Patent No. 0 352 244 A2 describes stabilized liquid detergent compositions using an amphoteric surfactant and European Patent No. 0 126 505 describes aqueous, enzymatic liquid detergent compositions which contain an enzyme-stabilizing system. The enzyme stabilizing system replaces polyols in known-enzyme stabilizing systems, based on mixtures of a polyol with a boron compound or with a reducing salt, with a dicarboxylic acid.

U.S. Pat. No. 5,356,800 describes a stabilizing formulation capable of enhancing the storage and shelf-life of liquid enzymatic compositions as well as acting as a dispersant aid for industrial process waters. The stabilizing formulation contains at least one water-soluble coupling agent selected from a short chain alcohol and a short chain glycol, at least one of (i) a polyethoxylated alkyl diamine and (ii) an amine oxide, and water. Also described is a stabilized liquid enzymatic composition which may contain one or more components of the stabilizing formulation and an enzyme. Methods for stabilizing a liquid enzymatic composition are also described.

Despite such efforts, some prior formulations and compositions were applicable to a limited number of enzyme types and/or were only able to stabilize enzymes or liquid enzymatic compositions over a relatively short period of time. Thus, there remains a need for formulations and compositions which can stabilize enzymes generally, without regard to the enzyme type or form.

Polyamide polymerization has been extensively developed by Carothers and co-workers (collected papers of Wallace H. Carothers, Vol. 1, High Polymers; Industrial Engineering Chemistry, 34:53 (1942), Bolton E.K.; Interscience, N.Y.). Superpolyamide, a high molecular weight or a highly polymerized fiber-forming polyamide, polymerization was developed by W. E. Hanford at E. I. du Pont de Nemours & Co. Inc. (U.S. Pat. No. 2,281,576). The generic term "nylon," as applied to this class of polyamides, refers to "any long chain synthetic polyamide which has reoccurring amide groups as an integral part of the main polymer chain, and which is capable of being formed into a filament in which the structural elements are oriented in the direction of the axis." (*Nylon Tech Manual,* E.I. du Pont de Nemours & Co. Inc., Wilmington, Del. (1952); R. E. Kirk, *Encyclopedia of Chemical Technology,* Vol. 10, (1953). Superpolyamide chemistry can be used in the preparation of fibers for use in textile arts such as, for example, knitted, woven, and pile fabrics, yams, ropes, cords, cloths, carpets, and clothing. These super hard, high melting point polyamides can also be used to produce wrapping foil, leather substitutes, gaskets, valves, washers, lampshades, bottle caps, belting, playing cards, fiber board substitutes, bookbinding, wire coatings and other similar products. However, while superpolyamides have been exploited in such a wide variety of uses, polyamide oligomers (e.g. pre-superpolyamide, pre-fiber-forming condensation polyamides, or precursors of superpolyamide and "nylon") have not found such wide application.

Polyamide oligomers have now been found to, in accordance with this invention, stabilize a wide variety of enzymes and enzymatic compositions over an extended period of time.

SUMMARY OF THE INVENTION

The invention provides a stabilized enzymatic composition. The stabilized enzymatic composition contains a polyamide oligomer and at least one enzyme. The polyamide oligomer is present in an amount effective for stabilizing the enzyme. The invention further provides a method of preparing a stabilized enzymatic composition. Such a method involves combining a polyamide oligomer and at least one enzyme. The polyamide oligomer is added in an amount effective to stabilize the enzyme. These and other features and advantages of the invention will be made more apparent from the following detailed description.

DETAILED DESCRIPTION OF THE INVENTION

One embodiment of the invention is a stabilized enzymatic composition. A stabilized enzymatic composition of the invention contains at least one polyamide oligomer and at least one enzyme. The polyamide oligomer is present in an amount effective to stabilize at least one enzyme of a liquid enzymatic composition.

To stabilize an enzyme, the invention employs a polyamide oligomer which may be any pre-superpolyamide or pre-fiber-forming polyamide oligomer. A pre-superpolyamide or pre-fiber-forming polyamide oligomer may be prepared by techniques known in the art including those described in U.S. Pat. No. 2,281,576 incorporated here in its entirety by reference. Preferably, in accordance with the invention, a polyamide oligomer is prepared via a condensation reaction of difunctional monomers capable of forming amide linkages. Kricheldorf, Hans R., *Handbook of Polymer Synthesis: Institute for Technical Macromolecular Chemistry,* University of Hamburg, Hamburg, Germany; Marcel Dekker (1992). During oligomer formation, each amide linkage is formed independently of the others. More preferably, in accordance with the invention, a polyamide oligomer is prepared via a fundamental condensation reaction of at least one dicarboxylic acid monomer and at least one diamine monomer as shown in Scheme 1:

Scheme 1

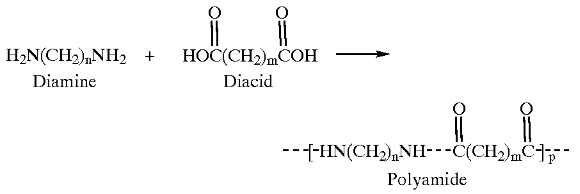

In Scheme 1, n is greater than or equal to 1, m is greater than or equal to 1, and p is preferably less than or equal to 70.

The fundamental condensation reaction may be a high or low thermal polycondensation reaction, including solution thermal polycondensation, melt polycondensation, or solid-state polycondensation. Preferably, in accordance with the invention, a polyamide oligomer is prepared by melt polycondensation. The condensation reaction may be performed under slight or moderate vacuum for removal of water.

When heat sensitive monomers are used to prepare a polyamide oligomer with a high melting point, care should be taken in the selection of a reaction process in order to minimize vaporization of the monomer supplied and of the oligomer or by-product produced. Low temperature polycondensation reaction conditions are preferably used to provide the activation energy of the reaction, the heat of neutralization of the monomer producing polyamide salts or nylon salts and/or of the resulting oligomer, and the heat of vaporization of the condensation by-product, which is water in most cases.

The diacid or dibasic acid monomer may be any synthetic or commercially available dicarboxylic acid. The diacid monomer may be hydrophobic, hydrophilic or both. Examples of suitable diacids include, but are not limited to, oxalic, malonic, glutaric, maleic, fumaric, terephthalic, and adipic acid. Preferably, the diacid is a $C_3$–$C_{10}$ nonaromatic diacid such as malonic, glutaric, maleic, fumaric, and adipic acid. The chemical formula of exemplary diacids are shown in Table 1.

TABLE 1

| Exemplary Dicarboxylic Acids | |
|---|---|
| oxalic acid | HO(O)CC(O)OH |
| malonic acid | $HO(O)C—CH_2—C(O)OH$ |
| glutaric acid | $HO(O)C—(CH_2)_3—C(O)OH$ |

TABLE 1-continued

| Exemplary Dicarboxylic Acids | |
|---|---|
| maleic acid | cis-HO(O)C—CH═CH—C(O)OH |
| fumaric acid | trans-HO(O)C—CH═CH—C(O)OH |
| terephthalic acid | $1,4\text{-}(C(O)OH)_2$-benzene |
| adipic acid | $HO(O)C—(CH_2)_4—C(O)OH$ |

The diamine monomer may be any synthetic or commercially available primary or secondary diamine. Preferably, the diamine monomer is a $C_1$–$C_{10}$ diamine. Examples of suitable diamines include, but are not limited to, 1,2-diaminoethane, 1,3-diaminopropane, 1,4-diaminobutane, 1,5-diaminopentane, 1,6-diaminohexane, 1,8-diaminooctane, 1,10-diaminodecane and diethylene triamine. Preferably the diamine is a linear (i.e. primary) and saturated diamines. More preferably, the diamine is a linear and saturated $C_2$–$C_3$ diamine, e.g. 1,2-diaminoethane and 1,3-diaminopropane. Exemplary diamines are shown in Table 2.

TABLE 2

| Exemplary Diamines | |
|---|---|
| 1,3-diaminopropane | $H_2N—(CH_2)_3—NH_2$ |
| 1,2-diaminoethane | $H_2N—(CH_2)_2—NH_2$ |
| 1,6-diaminohexane | $H_2N—(CH_2)_6—NH_2$ |
| diethylenetriamine | $H_2N—(CH_2)_2—NH—(CH_2)_2—NH_2$ |

Any combination of diamine or diacid, both as described above, is envisioned by the present invention as long as a polyamide oligomer or a reversible superpolyamide oligomer may be formed. When oxalic acid is used to form a polyamide oligomer, additional precautions should be taken since the reaction is strongly exothermic. Such precautions are well known in the art and include, for example, slow introduction of oxalic acid to the diamine and maintenance and monitoring of reaction temperature.

A homogenous polyamide oligomer may be prepared by the condensation of one type of diacid and one type of diamine. A heterogenous polyamide oligomer may be prepared by the condensation of more than one type of diacid and one type of diamine, more than one type of diamine and one type of diacid, or a combination thereof. Alternatively, a polyamide oligomer may be prepared from self-condensation of a difunctional monomer having both an amine moiety and an acid moiety.

In general, to prepare a polyamide oligomer useful in the invention, equimolar amounts of a diacid monomer and a diamine monomer are used in the condensation reaction. However, it is preferable that a slight molar excess of acid ranging from about 1.1–1.4 moles be present to produce product solutions having an acidic pH, preferably, a pH ranging between about 5.0 to about 7.0. More preferably, the pH ranges between about 6.0–6.8. The pH may be adjusted in situ before or during polyamide oligomer formation or after polyamide oligomer formation. Preferably, pH is adjusted in situ during polyamide oligomer formation.

The temperature at which the condensation reaction is conducted will vary depending upon the diamine or dibasic acid used. In general, the reaction temperature is such that superpolyamide oligomer formation is prevented. Preferably, during the initial addition of the reactant monomers, the reaction temperature is maintained at about 50–70° C. After completion of the addition of the reactant monomers, the reaction temperature is maintained at a temperature above about 100° C. Preferably, at this point, the reaction temperature is maintained at a temperature of about 110–140° C. Upon polyamide oligomer formation, as a result of the exothermic nature of the formation reaction, the reaction temperature rises to and generally is maintained at about 155–165° C. The reaction is maintained at this temperature until polyamide oligomer formation is complete or just before superpolyamide formation begins.

In practice, superpolyamide formation may be evaluated qualitatively by a glass rod test as described in U.S. Pat. No. 2,281,576, incorporated here by reference. The production of a pre-fiber-forming oligomer or pre-superpolyamide polymer is easily tested by merely touching the surface of the molten polymer with a glass rod and observing the elasticity of the molten polymer filaments or fibers drawn upon removal of the glass rod from the molten polymer. Prior to the fiber forming stage or superpolyamide stage, such filaments or fibers are quite elastic, i.e. retract readily into the molten polymer reaction mixture. Upon superpolyamide formation, elasticity is lost and the filaments or fiber are brittle or hard. Reversal of superpolyamide formation may be achieved by the addition of water to the reaction mixture. Quantitatively, measurements known in the art such as, for example, viscosity measurements, can be made to determine at which point heating of the reactants should be discontinued in order to avoid superpolyamide or fiber formation. Preferably viscosity values range between about 25,000 Cp–100,000 Cp. The viscosity value or range of the polyamide oligomer may be prechosen depending on the state of the enzyme to be stabilized. If the enzyme to be stabilized is in a non-fluid state as discussed below, preferably the polyamide oligomer will have a lower viscosity value, generally ranging between about 25,000–35,000 Cp. If a fluid state enzyme as discussed below is to be added, the polyamide oligomer may have a higher viscosity value, preferably ranging between about 50,000–100,000 Cp.

Upon polyamide oligomer formation, heating of the reaction is discontinued and the polyamide oligomer is allowed to cool to ambient temperature. In a preferred embodiment, heating is discontinued and a viscosity controlling agent such as a rheological conditioning agent is added to the molten reaction mixture. The viscosity controlling agent or rheological conditioning agent allows compositions of the invention containing a polyamide oligomer to maintain liquid flow characteristics such as pliability and malleability at temperatures upon cooling and until well below freezing. Examples of suitable viscosity controlling agents include, water and various rheological conditioning agents such as resins, aliphatic amides, polyamide esters, polyesters, and plasticizers such as glycols, glycerol, polyhydric alcohols, esters of ether alcohols, amines, diamines, dicarboxylic acids, cellulose derivatives, pyrrolidones, and polyvinylpyrrolidone. Preferably, water or a water/glycerol mixture is added to the molten reaction mixture. More preferably, a water/glycerol mixture is added to the molten reaction mixture as a 1:3 water/glycerol mixture. To achieve desired flow characteristics, the viscosity controlling agent may generally be added in amounts up to about 20% by weight based on the total weight of the final stabilized enzymatic composition.

At ambient temperature, the resulting solid polyamide oligomer exhibits thermoplastic properties. A preferred polyamide oligomer for stabilizing at least one enzyme may be clear, transparent, pliable and tacky to touch. If a plasticizer has been added, the polyamide oligomer may also be very glossy. Polyamide oligomer plasticized resins also exhibit excellent moisture vapor transmission resistance properties.

According to the invention, upon completion of polyamide oligomer formation as described, an enzyme may then be added to, or mixed with the polyamide oligomer, to form a stabilized enzymatic composition. Any type or class of enzyme may be stabilized using the polyamide oligomer. Particularly preferred enzymes are those previously discussed. The enzyme may be water-soluble, water-dispersible, water-emulsifiable, water-extractable or water insoluble. The enzyme may be in a fluid or non fluid state. Examples of a non-fluid state enzymes include, but are not limited to, powdered, prilled, granulated, microencapsulated, microcrystalline, membrane bound, particulate adsorbed or particulate grafted enzymes and the like. Preferably, if a non-fluid enzyme is used, it is first made soluble by techniques known in the art. Preferably, the non-fluid enzyme is made soluble by mixture with water/hydric alcohol solution. The enzyme may also be any pre-formulated liquid enzymatic composition, including any commercially available pre-formulated liquid enzymatic composition. The pre-formulated liquid enzymatic composition may be a water-based composition or formulated or employed in an organic solvent or medium.

Upon addition of the enzyme to a polyamide oligomer, the resulting mixture is generally agitated or stirred by techniques known in the art to form a homogeneous dispersion or blend. As a result of enzyme addition, the viscosity of the stabilized enzymatic composition may decrease to give a composition with desired viscosity or flow characteristics as discussed above.

In a stabilized enzymatic composition of the invention, a polyamide oligomer is present in an amount effective to stabilize at least one enzyme. Generally, a stabilized enzymatic composition of the invention contains about 0.1 to about 99% by weight of a polyamide oligomer as described above based on the total weight of the enzymatic composition. Preferably, a stabilized enzymatic composition of the invention contains about 25 to about 95% by weight of the polyamide oligomer. More preferably, the polyamide oligomer makes up about 50% by weight or greater of the stabilized enzymatic composition.

A "stabilized enzyme" is defined as an enzyme as described above which in the presence of a polyamide oligomer retains greater activity over its native state at a defined temperature. Preferably, a "stabilized enzyme" exhibits about 70% activity or greater after two weeks at 50° C. More preferably, a "stabilized enzyme" exhibits about 80% activity or greater after 16 weeks at 50° C.

Depending upon the enzyme and its intended use, the stabilized enzymatic composition generally has a final pH range of about 5.0 to about 7.0. Preferably, the pH of the composition ranges from about 6.0–6.8. As understood in the art, adjustment of pH may be necessary with a small amount of acid or alkaline material.

The stabilized enzymatic composition may contain other additives as known in the art directed toward the use of the composition in a particular industrial process. For example, the stabilized enzymatic composition may contain additives such as a surfactant, an emulsifier, a defoamer, and the like.

Due to the solubility of a polyamide oligomer in water and organic solvents, a stabilized enzymatic composition of the invention may be added directly to a system in which a particular enzyme is to be used. The enzyme may be dispersed directly into the system by agitation, such as stirring. Alternatively, the enzyme may be delivered to the system over time by allowing the polyamide oligomer to dissolve at its own rate within the system. In other uses, the enzyme may be liberated from the stabilized composition by dissolving away the polyamide oligomer using solvents containing hydroxyl groups such as, for example, water, glycols or hydric alcohols such as glycerol, or mixtures thereof. The resulting composition may then be used in the same manner as other enzyme compositions.

Another embodiment of the invention is a method for the preparation of a stabilized enzymatic composition as described above. The method of the invention relates the step of adding at least one enzyme to at least one polyamide oligomer prepared as described above. The combination forms a stabilized enzymatic composition where the polyamide oligomer is present in an amount effective to stabilize the enzyme as described above. The enzyme may be added to or combined with a polyamide oligomer either in its native state or as a pre-formulated liquid enzymatic composition as described above. As defined above, the enzyme is stabilized when, in the presence of the polyamide oligomer, the enzyme exhibits greater activity over its native state at a defined temperature. Additives as described above, if used, may be added at any time. Preferably, the additive is incorporated after the enzyme has been added to the polyamide oligomer.

The following examples are given to illustrate the present invention. It should be understood, however, that the invention is not to be limited to the specific conditions or details described in these examples.

EXAMPLE 1

General Procedure for Synthesizing a Polyamide Oligomer

In a reaction vessel, a solid diacid (1.2–1.4 mol) was added to a liquid diamine (1 mol). During addition of the diacid, the reaction vessel was maintained at a temperature of 50°–70° C. Table 3 lists specific diacid/diamine combinations and stoichiometries. Once addition was complete, the temperature of the reaction vessel was maintained at a temperature of 110°–140° C. until the diacid melted and various salt complexes resulting from the acid/base reaction formed. Upon melting of the diacid and formation of the salt complexes, a significant increase in temperature to 155°–165° C. was observed. The temperature of the reaction was then maintained at about 162° C. for 0.3 to 2.5 hours until the salt complexes underwent melt polycondensation and formed the desired polyamide oligomer. The condensation reaction was performed under slight to moderate vacuum for the removal of water.

Formation of the polyamide oligomer or pre-superpolyamide was determined by testing the fiber forming properties of the reaction mixture with a glass rod, i.e. the glass rod test (U.S. Pat. No. 2,281,576). After melt polycondensation had begun, every few minutes a glass rod was placed in the reaction mixture or solution and withdrawn briskly to form fine hairlike polymer threads which at the polyamide oligomer stage would retract back into the reaction solution due to the polymer's elastic properties. Heating of the reaction solution was continued for 1.5–2.0 hours until, as ascertained by the glass rod test, the polymer threads began to lose their elasticity, become brittle and fail to retract back into the reaction solution—an indication of the formation of superpolyamide or pre-fiber forming oligomer. Upon superpolyamide formation, water was added to the reaction solution until the glass rod test indicated the return of elasticity to the polymer threads. The reaction was quenched by removing the heat source and adding small amounts of no greater than 20 wt % of the solution weight of either water or a water/glycerol mixture having a ratio of 1 part water to 3 parts glycerol.

TABLE 3

Diacid and Diamine Combinations for Polyamide Oligomer Preparation

| Acid* | F.W. (g/mol) | Amount Acid (gm) | Base** | F.W. (g/mol) | Amount Base (gm) | Acid:Base Molar Ratio |
|---|---|---|---|---|---|---|
| oxalic | 90 | 108; 117; 126 | 1,3-diamino propane | 74 | 74 | 1.2:1; 1.3:1; 1.4:1 |
| | | 108; 117; 126 | 1,2-diamino ethane | 60 | 60 | 1.2:1; 1.3:1; 1.4:1 |
| malonic | 104 | 124; 135; 145 | 1,3-diamino propane | 74 | 74 | 1.2:1; 1.3:1; 1.4:1 |
| | | 124; 135; 145 | 1,2-diamino ethane | 60 | 60 | 1.2:1; 1.3:1; 1.4:1 |
| adipic | 146 | 175; 190; 204 | 1,3-diamino propane | 74 | 74 | 1.2:1; 1.3:1; 1.4:1 |
| | | 175; 190; 204 | 1,2-diamino ethane | 60 | 60 | 1.2:1; 1.3:1; 1.4:1 |
| | | 180; 195; 210 | 1,2-diamino hexane | 116 | 116 | 1.2:1; 1.3:1; 1.4:1 |
| fumaric | 116 | 139; 150; 162 | 1,3-diamino propane | 74 | 74 | 1.2:1; 1.3:1; 1.4:1 |
| | | 139; 150; 162 | 1,2-diamino ethane | 60 | 60 | 1.2:1; 1.3:1; 1.4:1 |
| maleic | 116 | 139; 150; 162 | 1,3-diamino propane | 74 | 74 | 1.2:1; 1.3:1; 1.4:1 |
| | | 139; 150; 162 | 1,2-diamino ethane | 60 | 60 | 1.2:1; 1.3:1; 1.4:1 |
| terephthalic | 166 | 200; 218; 232 | 1,3-diamino propane | 74 | 74 | 1.2:1; 1.3:1; 1.4:1 |
| | | 200; 218; 232 | 1,2-diamino ethane | 60 | 60 | 1.2:1; 1.3:1; 1.4:1 |
| glutaric | 132 | 158; 171; 184 | 1,3-diamino propane | 74 | 74 | 1.2:1; 1.3:1; 1.4:1 |

TABLE 3-continued

| Diacid and Diamine Combinations for Polyamide Oligomer Preparation | | | | | | |
|---|---|---|---|---|---|---|
| Acid* | F.W. (g/mol) | Amount Acid (gm) | Base** | F.W. (g/mol) | Amount Base (gm) | Acid:Base Molar Ratio |
| | | 158; 171; 184 | 1,2-diamino ethane | 60 | 60 | 1.2:1; 1.3:1; 1.4:1 |

*Acids available from Sigma Chemical Company of St. Louis, Mo.
**Bases available from Fisher Scientific of Norcross, Ga.

EXAMPLE 2

General Procedure for the Preparation of Stabilized Enzymatic Compositions

An enzyme at its original manufactured concentrate in either solid or liquid form is added to a polyamide oligomer prepared according to Example 1. Upon addition, the resulting mixture is agitated or stirred until a homogeneous dispersion is achieved. The enzyme is added to a polyamide oligomer such that the enzyme is present in an amount of 50% by weight or less based on the total weight of the composition.

EXAMPLE 3

Stabilization of Enzyme Compositions

The enzymatic stability at 50° C. of several stabilized enzymatic compositions was determined by measuring the % activity of the enzyme at 2, 4, 8, and 16 week intervals and compared to the enzymatic stability at 50° C. of the corresponding enzyme at its original manufactured concentrate, i.e. in the absence of a polyamide oligomer. The results are summarized in Tables 5–8. Percentages other than % activity express the % by weight of the total composition of each component of the stabilized enzymatic composition.

Each polyamide oligomer was prepared according to Example 1. Each stabilized enzymatic composition was prepared according to Example 2. Several polyamide oligomers were used to prepare the stabilized enzymatic compositions and are summarized in Table 4. The enzymes used to prepare the stabilized enzymatic compositions were at their original manufactured concentrate and include the following: PRIMATAN®, an alkaline protease from Genencor Inc. (Table 5); PULPZYME HC™, a xylanase from Novo-Nordisk Inc. (Table 6); MAXAMYL WL™, an amylase from International Bio-synthetics Inc.(Table 7); and Cellulase extracted from *Penicillium funiculosum* (P.f.) (Table 8).

TABLE 4

| Key for Polyamide Oligomers: | |
|---|---|
| Ex. | Polyamide Oligomer |
| A | a copolymer of oxalic acid and 1,3-diaminopropane |
| B | a copolymer of malonic acid and 1,3-diaminopropane |
| C | a copolymer of glutaric acid and 1,3-diaminopropane |
| D | a copolymer of maleic acid and 1,3-diaminopropane |
| E | a copolymer of fumaric acid and 1,3-diaminopropane |
| F | a copolymer of terephthalic acid and 1,3-diaminopropane |
| G | a copolymer of adipic acid and 1,3-diaminopropane |
| H | a copolymer of adipic acid and 1,3-diaminopropane and 1,2-diaminoethane |
| I | a copolymer of adipic acid and diethylenetriamine |
| J | a copolymer of adipic acid and 1,6-diaminohexane |

TABLE 5

| PRIMATAN ® Enzymatic Stability at 50° C. | | | | | |
|---|---|---|---|---|---|
| Enzymatic Composition | | % Activity Present After Week No. | | | |
| Polymer | Enzyme | 2 | 4 | 8 | 16 |
| A/50% | PRIMATAN ®/50% | <21 | <1 | — | — |
| None | PRIMATAN ®/Conc | <1 | — | — | — |
| B/50% | PRIMATAN ®/50% | >98 | >98 | >87 | >74 |
| C/50% | PRIMATAN ®/50% | >98 | >98 | >97 | >95 |
| D/50% | PRIMATAN ®/50% | >98 | >98 | >94 | >90 |
| E/50% | PRIMATAN ®/50% | >98 | >96 | >94 | >89 |
| F/50% | PRIMATAN ®/50% | <26 | <3 | — | — |
| G/50% | PRIMATAN ®/50% | >98 | >98 | >98 | >95 |
| H/50% | PRIMATAN ®/50% | >98 | >98 | >98 | >95 |
| I/50% | PRIMATAN ®/50% | >77 | >41 | — | — |
| J/50% | PRIMATAN ®/50% | >82 | >66 | <58 | — |

TABLE 6

| PULPZYME HC ™ Enzymatic Stability at 50° C. | | | | | |
|---|---|---|---|---|---|
| Enzymatic Composition | | % Activity Present After Week No. | | | |
| Polymer | Enzyme | 2 | 4 | 8 | 16 |
| A/50% | PULPZYME HC ™/50% | <34 | <11 | — | — |
| None | PULPZYME HC ™ | <12 | <1 | — | — |
| C/50% | PULPZYME HC ™/50% | >98 | >98 | >96 | >91 |
| D/50% | PULPZYME HC ™/50% | >98 | >98 | >93 | >86 |
| E/50% | PULPZYME HC ™/50% | >98 | >98 | >90 | >84 |
| F/50% | PULPZYME HC ™/50% | <28 | <1 | — | — |
| G/50% | PULPZYME HC ™/50% | >98 | >98 | >96 | >92 |
| H/50% | PULPZYME HC ™/50% | >98 | >98 | >91 | >88 |
| I/50% | PULPZYME HC ™/50% | >83 | >75% | <42% | — |
| J/50% | PULPZYME HC ™/50% | >85 | >70 | <47 | — |

TABLE 7

| MAXAMYL WL ™ Enzymatic Stability at 50° C. | | | | | |
|---|---|---|---|---|---|
| Enzymatic Composition | | % Activity Present After Week No. | | | |
| Polymer | Enzyme | 2 | 4 | 8 | 16 |
| A/50% | MAXAMYL WL ™/50% | <29 | <8 | — | — |
| None | MAXAMYL WL ™ | <4 | <1 | — | — |
| G/50% | MAXAMYL WL ™/50% | >98 | >98 | >95 | >86 |
| H/50% | MAXAMYL WL ™/50% | >98 | >98 | >90 | >85 |
| I/50% | MAXAMYL WL ™/50% | >89 | >72 | <37 | — |

TABLE 8

Cellulase P.f. Enzymatic Stability at 50° C.

| Enzymatic Composition | | % Activity Present After Week No. | | | |
|---|---|---|---|---|---|
| Polymer | Enzyme | 2 | 4 | 8 | 16 |
| None | Cellulase P.f./2% | <1 | — | — | — |
| C/98% | Cellulase P.f./2% | >98 | >98 | >87 | — |
| G/98% | Cellulase P.f./2% | >98 | >98 | >91 | — |
| J/98% | Cellulase P.f./2% | >73 | <32 | — | — |

EXAMPLE 4

Stabilization of Enzyme Compositions from a Non-fluid Enzyme

Many enzymes are manufactured as powders, prills, granulations, microcrystallines or as other non-fluid states. Often it would be advantageous to convert the solid material to a stabilized dispersible fluid state for ease of handling and utility. This change of phase or state allows for pumping and automated delivery systems to administer the enzyme solution without human handling or dusting of a powder. However, the stability of the enzyme must be assured. The following data (Table 9) relates stabilization of a lipase enzyme after extraction from its granular carrier to a fluid state.

Stabilized enzymatic compositions were prepared by using the enzyme LIPOMAX®, a lipase from Gist-Brocades Inc., at its original manufactured concentrate and at least one polyamide oligomer of F, G and H (see Table 4) or polyvinylpyrrolidine (PVP). The enzymatic stability at 50° C. of each stabilized enzymatic composition was determined by measuring the % activity of the enzyme at 2, 4, 8, and 16 week intervals and compared to the enzymatic stability at 50° C. of the original manufactured concentrate of LIPOMAX D, The percentages, other than % activity, given express the % by weight of the total composition of each component of the stabilized enzymatic composition.

TABLE 9

LIPOMAX ® Enzymatic Stability at 50° C.

| Enzymatic Composition | | % Activity Present After Week No. | | | |
|---|---|---|---|---|---|
| Polymer | Enzyme | 2 | 4 | 8 | 16 |
| PVP/10% | LIPOMAX ®/2% | >98 | >96 | >92 | >67 |
| None | LIPOMAX ®/2% | >98 | >55 | <1 | — |
| G/98% | LIPOMAX ®/2% | >98 | >98 | >97 | >90 |
| F/98% | LIPOMAX ®/2% | >35 | <14 | <1 | — |
| H/50% | LIPOMAX ®/2% | >98 | >98 | >94 | >88 |

EXAMPLE 5

Polymeric enzymatic compositions and enzyme concentrates of GREASEX 100L™, a liquid lipase from Novo-Nordisk Inc., were subjected to freeze/thaw cycles followed by an assay of % enzymatic activity remaining after each cycle. The stabilized enzymatic compositions retained their liquid flow characteristics down to −25° C. before freezing and even after four freeze/thaw cycles these compositions displayed greater than 95% activity remaining. Further, it was observed that even one freeze/thaw cycle significantly inactivated the enzyme concentrates. The results are presented in Table 10:

TABLE 10

GREASEX 100L ™** % Activity after Freeze/Thaw Cycle

| Enzymatic Composition | | % Activity at Freeze/Thaw Cycle No | | | |
|---|---|---|---|---|---|
| Polymer | Enzyme | 1 | 2 | 3 | 4 |
| C/50% + plasticizer*/10% | GREASEX 100L ™**/ 40% | >98 | >98 | >98 | >98 |
| None | GREASEX 100L ™** conc. | >78 | >40 | <16 | <1 |
| G/50% + plasticizer*/10% | GREASEX 100L ™**/ 70% | >95 | >83 | <47 | <26 |
| G/50% + plasticizer*/10% | GREASEX 100L ™**/ 40% | >98 | >98 | >97 | >95 |
| J/50% + plasticizer*/10% | GREASEX 100L ™**/ 40% | >98 | >95 | >92 | >90 |

*In all formulations the plasticizer used was the hydric alcohol, glycerol
**GREASEX 100L ™ is a bacterial lipase manufactured by Novo-Nordisk Inc.

The claimed invention is:

1. A stabilized enzymatic composition comprising an admixture of at least one polyamide oligomer and at least one enzyme, wherein said polyamide oligomer is a pre-superpolyamide or pre-fiber-forming polyamide oligomer having a polymer chain backbone containing only secondary amide linkages within the polymer chain backbone and is present in an amount effective for stabilizing the enzyme.

2. A stabilized enzymatic composition of claim 1, wherein the polyamide oligomer is a condensation product polymer of at least one dibasic acid and at least one diamine.

3. A stabilized enzymatic composition of claim 2, wherein the dibasic acid is selected from the group consisting of a saturated and unsaturated $C_3$–$C_{10}$ dicarboxylic acid and the diamine selected from the group consisting of 1,2-diamineoethane, 1,3-diaminopropane, 1,4-diaminobutane, 1,5-diaminopentane, 1,6-diaminohexane, 1,8-diaminooctane and 1,10-diaminodecane.

4. A stabilized enzymatic composition of claim 3, wherein the dicarboxylic acid is selected from the group consisting of malonic acid, glutaric acid, maleic acid, fumaric acid, and adipic acid.

5. A stabilized enzymatic composition of claim 1, wherein the polyamide oligomer is present in an amount of about 0.1 to 99% by weight of the total composition.

6. A stabilized enzymatic composition of claim 1 further comprising a viscosity controlling agent selected from the group consisting of water and a rheological conditioning agent.

7. A stabilized enzymatic composition of claim 6, wherein said rheological conditioning agent is selected from the group consisting of a resin, an aliphatic amide, a polyamide ester, a polyester, and a plasticizer.

8. A stabilized enzymatic composition of claim 7, wherein said plasticizer is selected from the group consisting of a glycol, a glycerol, a polyhydric alcohol, an ester of ether alcohol, an amine, a diamine, a dicarboxylic acid, a cellulose derivative, a pyrrolidone, and a polyvinylpyrrolidone.

9. A stabilized enzymatic composition of claim 1, wherein the enzyme is water-soluble or water-dispersible.

10. A stabilized enzymatic composition of claim 9, wherein the enzyme is in a fluid or non-fluid state.

11. A stabilized enzymatic composition of claim 10, wherein the enzyme is in a non-fluid state selected from the group consisting of a powder, a prill, a granule, a microcrystal, and a particulate upon which the enzyme is adsorbed.

12. A stabilized enzymatic composition of claim 1, wherein said enzyme is a pre-formulated liquid enzymatic composition.

13. A stabilized enzymatic composition of claim 1, wherein the enzyme is a protease, xylanase, amylase, cellulase, or a lipase.

14. A method for the preparation of a stabilized enzymatic composition comprising the step of adding an enzyme to a polyamide oligomer to form an admixture of said polyamide oligomer and said enzyme wherein said polyamide oligomer is a pre-superpolyamide or pre-fiber-forming polyamide oligomer having a polymer chain backbone containing only secondary amide linkages within the polymer chain backbone and is present in an amount effective to stabilize the enzyme.

15. A method of claim 14, wherein the polyamide oligomer is a condensation product polymer of at least one dibasic acid and at least one diamine.

16. A method of claim 14, wherein the enzyme is a protease, xylanase, amylase, cellulase, or lipase.

17. A method of claim 14, wherein the polyamide oligomer is present in an amount of about 0.1 to 99% by weight of the total composition.

18. A method of claim 14, wherein the enzyme is added as a pre-formulated liquid enzymatic composition.

* * * * *